(12) United States Patent
Trivedi et al.

(10) Patent No.: US 8,753,820 B2
(45) Date of Patent: Jun. 17, 2014

(54) PROTEIN BIOMARKERS FOR SOFT TISSUE DISEASE DIAGNOSIS AND AS THERAPEUTIC TARGETS FOR ORAL CARE INTERVENTION

(75) Inventors: Harsh M. Trivedi, Hillsborough, NJ (US); Tao Xu, Newton, MA (US); Ying Yang, Monmouth Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/262,038

(22) PCT Filed: Apr. 1, 2010

(86) PCT No.: PCT/US2010/029674
§ 371 (c)(1),
(2), (4) Date: Sep. 29, 2011

(87) PCT Pub. No.: WO2010/115034
PCT Pub. Date: Oct. 7, 2010

(65) Prior Publication Data
US 2012/0028261 A1    Feb. 2, 2012

Related U.S. Application Data

(60) Provisional application No. 61/165,674, filed on Apr. 1, 2009.

(51) Int. Cl.
*C12Q 1/68* (2006.01)
*G01N 33/52* (2006.01)

(52) U.S. Cl.
USPC ...................................................... 435/6.12

(58) Field of Classification Search
None
See application file for complete search history.

(56) References Cited

U.S. PATENT DOCUMENTS

| | | |
|---|---|---|
| 3,538,230 A | 11/1970 | Pader et al. |
| 4,358,437 A | 11/1982 | Duke |
| 5,288,480 A | 2/1994 | Gaffar et al. |
| 5,578,295 A | 11/1996 | Francis et al. |
| 5,703,123 A | 12/1997 | Pelzer et al. |
| 7,005,225 B2 | 2/2006 | Qian et al. |
| 7,005,255 B2 | 2/2006 | Kaddurah-Daouk et al. |
| 7,329,489 B2 | 2/2008 | Kaddurah-Daouk et al. |
| 7,550,258 B2 | 6/2009 | Kaddurah-Daouk et al. |
| 7,635,556 B2 | 12/2009 | Kaddurah-Daouk et al. |
| 2004/0224876 A1 | 11/2004 | Jost-Price et al. |
| 2005/0014132 A1 | 1/2005 | Kaddurah-Daouk et al. |
| 2005/0113345 A1 | 5/2005 | Chow et al. |
| 2006/0134676 A1 | 6/2006 | Kaddurah-Daouk et al. |
| 2006/0134677 A1 | 6/2006 | Kaddurah-Daouk et al. |
| 2006/0134678 A1 | 6/2006 | Kaddurah-Daouk et al. |
| 2006/0141421 A1 | 6/2006 | Braunecker et al. |
| 2007/0072203 A1 | 3/2007 | Kaddurah-Daouk et al. |
| 2007/0160544 A1 | 7/2007 | Sreenivasan |
| 2008/0027146 A1 | 1/2008 | Fiorellini et al. |
| 2008/0199412 A1* | 8/2008 | Milanovich et al. ............ 424/49 |

FOREIGN PATENT DOCUMENTS

| | | |
|---|---|---|
| EP | 0528468 | 2/1993 |
| EP | 1057809 | 12/2000 |
| EP | 1210928 | 6/2002 |
| EP | 1925292 | 5/2008 |
| GB | 2401865 | 11/2004 |
| WO | WO 95/13094 | 5/1995 |
| WO | WO 97/47282 | 12/1997 |
| WO | WO 01/48481 | 7/2001 |
| WO | WO 01/55386 | 8/2001 |
| WO | WO 01/85116 | 11/2001 |
| WO | WO 2005/039504 | 5/2005 |
| WO | WO 2005/057222 | 6/2005 |
| WO | WO 2005/103071 | 11/2005 |
| WO | WO 2008/093072 | 7/2008 |
| WO | WO 2009/048841 | 4/2009 |

OTHER PUBLICATIONS

Kim et al. (J Periodontol, 2005, 76:1735-1742).*
Toker et al. (Clin Oral Invest, 2006, 10:305-310).*
Pozo et al. (J Periodont Res, 2005, 40:199-207).*
HGF-1 ATCC CRL-2014, accessed Jun. 15, 2013.*
Beikler et al. (BMC Medical Genomics, 2008, vol. 1, p. 1-9).*
Afflitto et al., 1989, "Salivary and plaque triclosan levels after brushing with a 0.3% triclosan/copolymer/NaF dentifrice," Amer. J. Dent. 2:207-210.
Akalin et al., 2007, "Lipid Peroxidation Levels and Total Oxidant Status in Serum, Saliva and Gingival Crevicular Fluid in Patients with Chronic Periodontitis," J. Clin. Periodontol. 34(7):558-265.
Armitage, 2004, "Analysis of Gingival Crevice Fluid and Risk of Progression of Periodontitis," Periodontol. 34:109-119.
Back et al., 2007, "Increased Leukotriene Concentrations in Gingival Crevicular Fluid from Subjects with Periodontal Disease and Atherosclerosis," Atherosclerosis 193(2):389-394.
Bergamini et al., 2004, "Oxygen, Reactive Oxygen Species and Tissue Damage," Curr. Pharm. Des. 10(14):1611-1626.
Berry et al., 2004, "Xanthine Oxidoreductase and Cardiovascular Disease: Molecular Mechanisms and Pathophysiological Implications," J. Physiol. 555(Pt. 3):589-606.
Bodet et al., 2005, "Modulation of cytokine production by Porphyromonas gingivalis in a macrophage and epithelial cell coculture model," Microbes & Infect. 7(3):448-456.
Brantzaeg et al., 1992, "Compartmentalization of lipopolysaccharide production correlates with clinical presentation in meningococcal disease," J. Infect. Dis. 166(3):650-652.
Bunnell et al., 2000, "A lipid A analog, E5531, blocks the endotoxin response in human volunteers with experimental endotoxemia," Crit. Care Med. 28(8):2713-2720.
Cannon et al., 2008, "Salivary Metabonomics: A New Objective Measure in Oral Care," Poster 14, 8th European Symposium on Saliva, May 14-17, 2008, The Netherlands.

(Continued)

*Primary Examiner* — Stephanie K Mummert
(74) *Attorney, Agent, or Firm* — Howard C. Lee (57) ABSTRACT

Methods for identifying compounds useful for treating diseases or conditions of the oral cavity are described herein.

6 Claims, 1 Drawing Sheet

(56) References Cited

OTHER PUBLICATIONS

Chapple et al., 2002, "Glutathione in Gingival Crevicular Fluid and its Relation to Local Antioxidant Capacity in Periodontal Health and Disease," Mol. Pathol. 55(6):367-373.
Ciantar et al., 2002, "Development of an in vitro Microassay for Glucose Quantification in Submicrolitre Volumes of Biological Fluid," J. Periodontal Res. 387(2):79-85.
El Moudni et al., 1995, "Purification and characterisation of a metallopeptidase of *Candida albicans*," J. Med. Microbiol. 43(4):282-288.
Embery et al., 1994, "Gingival Crevicular Fluid: Biomarkers of Periodontal Tissue Activity," Adv. Dent. Res. 8(2):329-336.
Fokkema et al., 2003, "Monocyte-derived RANTES is intrinsically elevated in periodontal disease while MCP-1 levels are related to inflammation and are inversely correlated with IL-12 levels," Clin. & Exp. Immunol. 131(3):477-483.
Fothergill et al., 1977, "Catabolism of L-Lysire by *Pseudomonas aureuginosa*," J. Gen. Micriobiol. 99(1):139-155.
Gallegos Olea Olea et al., 2002, "Organic Carbonate from *Caloptropis proceru* Leaves," Fitoterapia 73(3):263-265.
Gaspersic et al., 2010, "Anti-NGF treatment reduces hone resorption in periodontitis," J. Dental Res. 89(5):515-520.
Golub et al., 1998, "Modulation of the Host Response in the Treatment of Periodontitis," Dent. Today 17(10):102-6, 108-9.
Golub et al., 1997, "A matrix metalloproteinase inhibitor reduces bone-type collatten degradation fragments and specific collagenases in gingival crevicular fluid during adult periodontitis," Inflamm. Res. 46:310-319.
Harrison, 2004, "Physiological Roles of Xanthine Oxidoreductase," Drug Metab. Rev. 36(2):363-375.
Heasman et al., 1993, "Changes in Crevicular Fluid Levels of Interleukin-1 Beta, Leukotriene B4, Prostaglandin E2, Thromboxane B2 and Tumour Necrosis Factor Alpha in Experimental Gingivitis in Humans," J. Periodontal Res. 28(4):241-247.
Holt et al., 2001, "Dental damage, sequelae, and prevention," Western J. of Medicine 174(4):288-290.
Ilgenli et al., 2006, "Gingival Crevicular Fluid Matrix Metalloproteinase-13 Levels and Molecular Forms in Various Types of Periodontal Diseases," Oral Dis. 12(6):573-579.
Imbert et al., 2002, "Effect of matrix metalloprotease inhibitors on the 95 kDa metallopeptidase of *Candida albicans*,"J. Antibicrob. Chemother. 49(6):1007-1010.
Ingman et al., 1996, "Matrix metalloprotemases and their inhibitors in gingival crevicular fluid and saliva of periodontitis patients," J. Clin. Periodontol. 23(12):1127-1132.
Ingman et al., 1994, "Multiple Forms of Gelatinases/Type IV Collagenases in Saliva and Gingival Crevicular Fluid of Periodontitis Patients," J. Clin. Periodontol. 21(1):26-31.
International Search Report and Written Opinion in International Application No. PCT/US10/029674 mailed Nov. 12, 2010.
International Search Report and Written Opinion in International Application No. PCT/US10/029670 mailed Aug. 12, 2010.
International Search Report and Written Opinion in International Application No. PCT/US09/039184 mailed Jun. 25, 2010.
International Search Report and Written Opinion in International Application No. PCT/US09/039140 mailed Nov. 27, 2009.
International Search Report and Written Opinion in International Application No. PCT/US07/060222 mailed Aug. 2, 2007.
Ishikura et al., 2003, "Cloning of the Tannerella Forsythensis (Bacteriodes Forsythus) siaH1 Gene and Purification of the Sialidase Enzyme," J. Med. Micriobiol. 52(Pt. 12):1101-1107.
Jackson et al., 2007, "The Production of Reactive Oxygen and Nitrogen Species by Skeletal Muscle," J. Appl. Physiol. 102(4):1604-1670.
Jahngen et al., 1984, "High-Performance Liquid Chromatography Analysis of Purine Nucleosides in Human Gingival Crevicular Fluid," Arch. Oral Biol. 29(8):607-610.
Kantarci et al., 2003, "Neutrophil-Mediated Tissue Injury in Periodontal Disease Pathogenesis: Findings from Localized Aggressive Periodontitis," J. Periodontal. 74(1):66-75.

Karthikeyan et al., 2007, "Gingival Crevicular Fluid and Serum Leptin: Their Relationship to Periodontal Health and Disease," J. Clin. Periodontol. 34(6):467-472.
Kiili et al., 2002, "Collagenase-2 (MMP-8) and collagenase-3 (MMP-13) in adult periodontitis: molecular forms and levels in gingival crevicular fluid and immunolocalisation in gingival tissue," J. Clin. Periodontal. 29(3):224-232; Erratum in: J. Clin. Periodontal. 2004, 31(2):149.
Lamster et al., 2007, "Analysis of Gingival Crevicular Fluid as Applied to the Diagnosis of Oral and Systemic Diseases," Ann. NY Acad. Sci. 1098:216-229.
Lamster, 1997, "Evaluation of Components of Gingival Crevicular Fluid as Diagnostic Tests," Ann. Periodontol. 2(1):123-137.
Lamster et al., 1987, "The Polyamines Putreseine, Spermidine and Spermine in Human Gingival Crevicular Fluid," Arch. Oral Biol. 32(5):329-333.
Lapp et al., 2005, "Analysis of interleukin-activated human gingival fibroblasts: modulation of chemokine responses by female hormones," J. Periodontol. 76(5):803-812.
Lawton et al., 2008, "Analysis of the Adult Human Plasma Metabolome," Pharmacogenomics 9(4):383-397.
Loos et al., 2005, "Host-Derived Diagnostic Markers for Periodontitis: Do They Exist in Gingival Crevice Fluid?" Periodontol. 39:53-72.
Lorencini et al., 2009, "Changes in MMPs and inflammatory cells in experimental gingivitis," Histol. Histopathol. 24(2):157-166.
Madianos et al., 2005, "Generation of inflammatory stimuli: how bacteria set up inflammatory responses in the gingiva," J. Clin. Periodontol. 32(Supp. 6):57-71.
Mahanonda et al., 2002, "Upregulation of co-stimulatory molecule expression and dendritic cell marker (CD83) on B cells in periodontal disease," J. Periodontal Res. 37(3):177-183.
Mantyla et al., 2003, "Gingival creviciuar fluid collagenase-2 (MMP-8) test stick for chair-side monitoring of periodontitis," J. Periodontol. Res. 38(4):436-439.
McAllister et al., 2008, "Spit Tests: Searching for Biomarkers in the Salivary Proteome," Poster 37, 8th European Symposium on Saliva, May 14-17, 2008, The Netherlands.
Modeer et al., 1996, "Triclosan reduces prostaglandin biosynthesis in human gingival fibroblasts challenged with interleukin-1 in vitro," J. Clin. Periodontol. 23(10):927-933.
Morisseau et al., 1999, "Potent Urea and Carbamate Inhibitors of Solble Epoxide Hydrolases," PNAS 96(16):8849-8854.
Nixon et al., 2000, "Cytokine responses to treponema pectinovorum and treponema denticola in human gingival fibroblasts," Infect. & Immun. 68(9):5284-5292.
Ogawa et al., 2002, "Cell activation by Porphyromonas gingivaits lipid A molecule through Toll-like receptor 4- and myeloid differentiation factor 88-dependent signaling pathway," Int. Immunol. 14(11):1325-1332.
Ozmeric, 2004, "Advances in Periodontal Disease Markers," Clin. Chim. Acta 343(1-2):1-16.
Pacher et al., 2006, "Therapeutic Effects of Xanthine Oxidases Inhibitors: Renaissance Half a Century after the Discovery of Allopurinol," Pharmacol. Rev. 58(1):87-114.
Page et al., 1991, "The role of inflammatory mediators in the pathogenesis of periodontal disease." J. Periodontol. Res. 26(3 Pt. 23:230-242.
Pihlstrom et al., 2005, "Periodontal Diseases," Lancet 366(9499):1809-1820.
Pozo et al., 2005, "Longitudinal analysis of metalloproteinases, tissue inhibitors of metalloproteinases and clinical parameters in gingival crevicular fluid from periodontitis-affected patients," J. Periodontol. Res. 40(3):199-207.
Pradeep et al., 2007, "Gingival Crevicular Fluid Levels of Neopterin in Healthy Subjects and in Patients with Different Periodontal Diseases," J. Periodontol. 78(10):1962-1967.
Prapulla et al., 2007: "Gingival Crevicular Fluid VEGF Levels in Periodontal Health and Disease," J. Periodontol. 78(9):1783-1787.
Preshaw et al., 2004, "Subantimicrobial dose doxycycline as adjunctive treatment for periodontitis. A review," J. Clin.. Periodontol. 31(9):697-707.

(56) References Cited

OTHER PUBLICATIONS

Putnins et al., 2002, "Induction of keratinocyte growth factor I Expression by lipopolysaccharide is regulated by CD-I4 and toll-like receptors 2 and 4," Infect. &. Immun. 70(12):6541-6548.

Qin et al., 2006, "Effect of Minocycline Hydrochloride Ointment on IL-8 in Gingival Crevicular Fluid," Wuhan Dune Xuebao [Medical journal of Wuhan University] 27(1):75-78.

Rodier et al., 1999. "A *Candida albicans* metallopeptidase degrades constitutive proteins of extracellular matrix," FEMS Microbiol. Lett. 177(2):205-210.

Rossomando et al., 1993, "A novel method for the detection of TNF-alpha in gingival crevicular fluid," J. Periodontol. 64(5 Suppl):445-449.

Ruwanpura et al, 2004, "Prostaglandin E2 regulates interieukin-1beta-induced matrix metalloproteinase-3 production in human gingival fibroblasts," J. Dental Res. 83(3):260-265.

Search Report from the European Patent Office for Corresponding European Patent Application No. EP 1015338 dated Aug. 3, 2010.

Segal et al., 2000, "Xanthine Oxidase Contributes to Host Defense against *Burkholderia cepacia* in the p47(phox−/−) Mouse Model of Chronic Granulomatous Disease." Infect. Immun. 68(4):2374-2378.

Seymour et al., 2007, "Relationship between. Periodontal Infections and Systemic Disease," Clin. Microbiol. Infect. 13(Suppl. 4):3-10.

Smalley, 1994, "Pathogenic Mechanisms in Periodontal Disease," Adv. Dent. Res. 8(2):320-328.

Sorsa et al., 1990, "The role of gingival crevicular fluid and salivary interstitial collagenases in human periodontal diseases," Arch. Oral Biol. 35 Suppl:193S-196S.

Stevens et al., 2000, "Antibacterial Properties of Xanthine Oxidase in Human Milk," Lancet 356(9232):829-830.

Sugawara, 2003, "Host Defense Mechanisms in Oral Mucosa," Tohoku University Dental Journal 22:11-18.

Sugawara et al., 2002, "Innate immune responses in oral mucosa," J. Endotoxin Res. 8(6):465-468.

Szasz et al., 2007, "A Comparison of Arteries and Veins in Oxidative Stress: Producers, Destroyers, Function, and Disease," Exp. Biol. Med. (Maywood) 232(1):27-37.

Taba et al., 2005: "Diagnostic Biomarkers for Oral and Periodontal Diseases," Dent. Clin. North Am. 49(3):551-571.

Tatakis et al., 2005, "Etiology and pathogenesis of periodontal diseases," Dent. Clin. N. Am. 49:491-516.

Teng et al., 1992, "Gingival crevicular fluid gelatinase and its relationship to periodontal disease in human subjects," J. Periodontal Res. 27(5):544-552.

Tervahartiala et al., 2000, "The in vivo Expression of the Collagenolytic Matrix Metalloproteinases (MMP-2, -8, -13, and -14) and Matrilysin (MMP-7) in Adult and Localized Juvenile Periodontitis," J. Dental Res. 79(12):1969-1977.

Toker et al., 2006, "EtTect of meloxicam on gingival crevicular fluid IL-beta and IL1 receptor antagonist levels in subjects with chronic periodontitis, and its effects on clinical parameters," Clin. Oral Investig. 10(4):305-310.

Tsai et al.: 2005, "Lipid Peroxidation: A Possible Role in the Induction and Progression of Chronic Periodontitis," J. Periodontal Res. 40(5):378-384.

Tu et al., 2009, "Cyclosporine A enhances apoptosis in gingival keratinocytes of rats and in OECM1 cells via the mitochondrial pathway," J. Periodontal Res. 44(6):767-775.

Uehara et al., 2002, "Priming of human oral epithelial cells by interferon-gamma to secrete cytokines in response to lipopolysaccharides lipoteichoic acids and peptidoglycans," J. Med. Microbiol. 51(8):626-634.

Uehara et al., 2001, "Contrasting responses of human gingival and colonic epithelial cells to lipopolysaccharides, lipoteichoic acids and peptidoglycans in the presence of soluble CD14," Med. Microbiol. Immunol. 189(4):185-192.

Valko et al., 2007, "Free Radicals and Antioxidants in Normal Physiological Functions and Human Disease," Int. J. Biochem. Cell Biol. 39(1):44-84.

Van Dyke et al., 2003, "Resolution of inflammation: A New Paradigm for the Pathogenesis of Periodontal Diseases," J. Dent. Res. 82(2):82-90.

Wang et al., 2002, "*Porphyromonas gingivalis* lipopolysaccharide signaling in gingival fibroblasts CD14 and Toll-like receptors," Crit. Rev. Oral Biol. Med. 13(2):132-142.

Weinberg et al., 1998, "Epithelial antimicrobial peptides: review and significance for oral applications," Crit. Rev. Oral Biol. Med. 9(4):399-414.

Xu et al., 2004: "Effectiveness of a Triclosan/Copolymer Dentifrice on Microbiological and Inflammatory Parameters," Compend. Contin. Educ. Dent., Medline Database Accession No. NLM15645886.

Yang et ai., 2006, "Eukaryotic Pathways for the Induction of Peptidase by Pathogenic Oral Bacteria," D-144, http://icg.ou.edu/ASM2006/data/papers/D_144.htm.

Yoshimura, 2004, "Recognition of Periodontopathic Bacteria by Innate Immune System," J. Japanese Soc. of Periodontol. 46:94-100.

Yoshioka et al., 2003, "Effect of hydroxamic acid-based matrix Metalloproteinase inhibitors on human gingival cells and Porphyronionas gingivalis," J. Periodontol. 74(8):1219-1224.

\* cited by examiner

PROTEIN BIOMARKERS FOR SOFT TISSUE DISEASE DIAGNOSIS AND AS THERAPEUTIC TARGETS FOR ORAL CARE INTERVENTION

CROSS-REFERENCE TO RELATED APPLICATIONS

The present application is a national stage entry under 35 U.S.C. §371 of International Patent Application No. PCT/US2010/029674, filed Apr. 1, 2010, which claims priority to U.S. Provisional Application No. 61/165,674, filed Apr. 1, 2009, the entireties of which are hereby incorporated by reference.

BACKGROUND

Periodontal disease is characterized, in part, by abnormal and excessive degradation of the periodontal organic matrix. This matrix includes the gingiva, periodontal ligament, cementum and alveolar bone. These events result in the clinical manifestation of periodontitis, including gingival recession, pocket formation, loss of attachment, and eventual tooth loss. Many different inflammatory mediators are produced by periodontal tissues affected by periodontal disease. Some of these mediators appear to play a central role in the destructive processes observed in cases of periodontal diseases, which has led some investigators to examine the possibility of using certain inflammatory mediators as biomarkers for progressive lesions (Sorsa, T. et al. Arch. Oral. Biol. 35: 193S-196S, 1990: Page, R. C., J. Periodont. Res. 26: 230-242, 1991).

SUMMARY

The invention includes a method for diagnosing periodontal disease in a mammal comprising: obtaining a gingival and/or saliva sample from the mammal, detecting the presence of a biomarker in the gingival sample, detecting the level of the biomarker in the sample, and diagnosing the organism with periodontal disease based on the level of the biomarker detected.

A biomarker is at least one member selected from the group consisting of FAS, IL-1B, IL-8, MMP-9, DEFB4, CTSS, IL-17B, CARD10, BGN, BE, IL-12A, IL-6, LCN8, LPO and MMP-13.

The invention also includes a method for diagnosing periodontal disease in a mammal comprising obtaining a gingival and/or saliva sample from the mammal, detecting the presence of a biomarker in the sample, detecting the level of the biomarker in the sample, comparing the level of biomarker in the sample to predetermined reference value correlating a level of biomarker with periodontal disease, and diagnosing the mammal with periodontal disease when the level of the biomarker in the sample corresponds to the level of biomarker that the reference value correlates with periodontal disease.

The invention also includes a method for diagnosing periodontal disease in a mammal comprising obtaining a gingival and/or saliva sample from the mammal, detecting the presence of a biomarker in the sample, detecting the level of the biomarker in the sample, comparing the level of biomarker in the sample to the level of the same biomarker in a control sample, wherein the mammal is diagnosed with periodontal disease when an altered level of the biomarker is detected in the sample relative to the control sample.

In an aspect, the level of biomarker is greater in the sample relative to the control sample.

The invention includes a panel of biomarkers for detecting periodontal disease in a mammal comprising two or more biomarkers selected from the group consisting of FAS, IL-1B, IL-8, MMP-9, DEFB4, CTSS, IL-17B, CARD10, BGN, BE, IL-12A, IL-6, LCN8, LPO and MMP-13, wherein the biomarkers are obtained from a gingival and/or saliva sample of a mammal diagnosed with periodontal disease.

The invention further includes a method for monitoring periodontal disease in a mammal comprising obtaining a first gingival and/or saliva sample from the mammal at a first point in time, obtaining a second gingival and/or saliva sample from the mammal at a second point in time, detecting the presence of at least one biomarker in the first and second samples, detecting the level of the at least one biomarker in the first and second samples, and comparing the level of biomarker in the first and second samples, wherein a decrease of the level of the biomarker in the second sample relative to the first sample indicates a decrease in periodontal disease in the mammal.

The invention includes a method for treating periodontal disease in a mammal comprising contacting a cell with an agent that down-regulates at least one biomarker selected from the group consisting of FAS, IL-1B, IL-8. MMP-9, DEFB4, CTSS, IL-17B, CARD10, BGN, BE, IL-12A, IL-6, LCN8, LPO and MMP-13, wherein the down-regulation of the biomarker(s) correlates with a reduction in at least one symptom associated with the periodontal disease.

The invention also includes a method of identifying a compound useful in treating periodontal disease in a mammal, the method comprising contacting a cell with a test compound and determining whether the test compound down-regulates at least one biomarker selected from the group consisting of FAS, IL-1B, IL-8, MMP-9, DEFB4, CTSS, IL-17B, CARD10, BGN, BE, IL-12A, IL-6, LCN8, LPO and MMP-13, wherein the down-regulation of biomarker(s) is an indication that the test compound is useful to treat periodontal disease.

The invention further includes a method for diagnosing gingivitis in a mammal comprising obtaining a gingival and/or saliva sample from the mammal, detecting the presence of a biomarker in the sample, detecting the level of the biomarker in the sample, diagnosing the organism with gingivitis based on the level of the biomarker detected.

The invention also includes a method for diagnosing gingivitis in a mammal comprising obtaining a gingival and/or saliva sample from the mammal, detecting the presence of a biomarker in the sample, detecting the level of the biomarker in the sample, comparing the level of biomarker in the sample to predetermined reference value correlating a level of biomarker with gingivitis, and diagnosing the mammal with gingivitis when the level of the biomarker in the sample corresponds to the level of biomarker that the reference value correlates with gingivitis.

The invention also includes a method for diagnosing gingivitis in a mammal comprising obtaining a gingival and/or saliva sample from the mammal, detecting the presence of a biomarker in the sample, detecting the level of the biomarker in the sample, and comparing the level of biomarker in the sample to the level of the same biomarker in a control sample, wherein the mammal is diagnosed with gingivitis when an increased level of the biomarker is detected in the gingival and/or saliva sample relative to the control sample.

The invention includes a method for monitoring gingivitis in a mammal comprising obtaining a first gingiva and/or saliva 1 sample from the mammal at a first point in time, obtaining a second gingival and/or saliva sample from the mammal at a second point in time, detecting the presence of at least one biomarker in the first and second samples, detecting a level of the at least one biomarker in the first and second samples, and comparing the level of biomarker in the first and second samples, wherein a decrease of the level of the biomarker in the second sample relative to the first sample indicates a decrease in gingivitis in the mammal.

The invention also includes a method for treating gingivitis in a mammal comprising contacting a cell with an agent that down-regulates at least one biomarker selected from the group consisting of FAS, IL-1B, IL-8, MMP-9, DEFB4, CTSS, IL-17B, CARD10, BGN, BE, IL-12A, IL-6, LCN8, LPO and MMP-13, wherein the down-regulation of the at least one biomarker correlates with a reduction in at least one symptom associated with the gingivitis. In an aspect, the level of biomarker returns to a level accepted as normal. In another aspect, the level of biomarker returns to a baseline level.

The invention further includes a method of identifying a compound useful in treating gingivitis in a mammal, the method comprising contacting a cell with a test compound and determining whether the test compound down-regulates at least one biomarker selected from the group consisting of FAS, IL-1B, IL-8, MMP-9, DEFB4, CTSS, IL-17B, CARD10, BGN, BE, IL-12A, IL-6, LCN8, LPO and MMP-13, wherein the down-regulation of at least one of the biomarkers is an indication that the test compound is useful to treat gingivitis.

DETAILED DESCRIPTION

What are needed in the art are diagnostic and/or prognostic tests for the levels of biomarkers, including biomarkers that are elevated in a periodontal disease state. Such biomarkers include FAS, IL-1B, IL-8, MMP-9, DEFB4, CTSS, IL-17B, CARD10, BGN, BE, IL-12A, IL-6, LCN8, LPO and MMP-13. What are also needed in the art are diagnostic and/or prognostic tests for periodontal disease, which would assess the level of inflammatory mediators in a gingival sample, such as gingival crevicular fluid (GCF), or in a saliva sample. Further, treatments for periodontal disease in patients in need thereof, comprising inhibition of elevated levels of one or more of FAS, IL-1B, IL-8, MMP-9, DEFB4, CTSS, IL-17B, CARD10, BGN, BE, IL-12A, IL-6, LCN8, LPO and MMP-13, are also needed.

For example, matrix metalloprotease 13 (MMP-13; also known as CLG3) is a major destructive collagenase in periodontitis and periodontal disease. MMP-13 can be found in diseased periodontal tissue and gingival crevicular fluid, as well as in saliva. The level of this enzyme is positively correlated to periodontitis clinical indices. That is, elevated, or "above normal" levels of MMP-13 is an indication of periodontal disease. The measurement may be made of MMP-13 enzymes, RNA, or biological activity. Inhibition of the activity and/or presence of MMP-13 is useful for the treatment of periodontal disease.

The following biomarkers of periodontal disease as set forth herein can also be detected and/or the levels measured using the respective enzymes, proteins, RNA, or biological activity. Elevated or "above normal" levels of the following biomarkers, either alone or in conjunction with one or more of one another, is also indicative of periodontal disease. As for MMP-13, inhibition of the activity and/or presence of MMP-13 is useful for the treatment of periodontal disease:

FAS (also known as ALPS1A and APO-1) is involved in apoptosis, and forms "DISC," a death-inducing signaling complex upon binding ligand.

Interleukin 1-beta (IL-1B) is an inflammatory cytokine, involved in the mammalian immune response against infection.

Interleukin 8 (IL-8; also known as 3-10C and AMCF-1) is a member of the C—X—C chemokine family, and is involved in the induction of chemotaxis in target neutrophil gfanulocytes as part of the innate immune response.

Matrix metalloprotease 9 (MMP-9; also known as GELB and CLG4B) is a gelatinase which is also a major destructive matrix metalloprotease in periodontal disease.

Defensin beta 4 (DEFB4; also known as BETA2 and DEFB-2) is a defensin. DEFB4 is an antibiotic peptide regulated locally by inflammation.

Cathepsin S (CTSS; also known as MGC3886) a member of the C1 peptidase family, is a cysteine protease that plays a role in the presentation of antigenic proteins/peptides to MHCII class molecules.

Interleukin 17B (IL-17B; also known as IL-20) is an IL-17-related cytokine. IL-17B stimulates the release of IL-1B and TNF-alpha from monocytes.

Casspase recruitment domain family member 10 (CARD10; also known as BIMP1 and CARMA3) is involved in apoptosis signaling. CARD10 also activates NF-kappa-B and belongs to the membrane-associated guanylate kinase family.

Biglycan (BGN; also known as DSPG1 and PG-S1) is a matrix proteoglycan containing two attached glycosaminoglycan chains, and is related to decorin. It is believed to bind to collagen fibrils and transfer growth factor beta.

B-factor, properdin (BF; also known as CFAB and GBG) is a component of the alternative pathway of complement activation. The active subunit is a serine protease that is involved in the proliferation of preactivated B lymphocytes.

Interleukin 12A (IL-12A; also known as CLMF) is a cytokine that acts on T cells and natural killer cells, and is involved in the differentiation of both Th1 and Th2 cells, as well as the T-cell-independent induction of interferon gamma.

Interleukin 6 (IL-6; also known as BSF2 and HGF) is an immunoregulatory cytokine that activates a cell surface signaling complex. It acts as both a pro- and anti-inflammatory cytokine, and stimulates immune response to trauma, including response to foreign pathogens.

Lipocalin 8 (LCN8) belongs to a family of proteins involved in inflammation and detoxification process effected by immune system activation in mammals.

Lactoperoxidase (LPO; also known as SPO) is an antioxidant enzyme involved in host defense against infection.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

"Periodontal disease", as the term is used herein, encompasses periodontitis, gingivitis and gum disease.

"Gingivitis", as used herein, means inflammation of the gingival tissues, a condition in which inflammation is localized within the gingiva and no lesion occurs in the bone and periodontal ligament.

As used herein, the term "periodontitis" refers to abnormal and excessive degradation of the periodontal organic matrix, including the gingiva, periodontal ligament, cementum and alveolar bone. The clinical manifestation of periodontitis includes, but is not limited to, gingival recession, pocket formation, loss of matrix attachment, tooth and bone loss. Periodontitis may be characterized as early periodontitis, moderate periodontitis or advanced periodontitis. However, periodontitis should not be limited to only those symptoms and sequelae set forth herein, as will be understood by the skilled artisan. Early periodontitis is clinically manifested, among other symptoms, by one or more of: bleeding upon probing; the presence of pockets (3 to 4 mm); localized areas of recession; attachment loss (3 to 4 mm); bone loss (e.g., horizontal); and class I furcation invasion areas. Moderate periodontitis is clinically manifested, among other symptoms, by one or more of: the presence of pockets (4 to 6 mm); the presence of attachment loss (4 to 6 mm); bleeding upon probing; grade I and/or grade II furcation invasion areas; class I tooth mobility; bone loss (e.g., horizontal and/or vertical); and loss of $\frac{1}{3}$ of supporting alveolar bone (i.e., crown to root ratio of 1:1). Advanced periodontitis is clinically manifested by one or more of: bleeding upon probing; the presence of pockets (over 6 mm); attachment loss (over 6 mm); grade II and/or grade III furcation invasion areas; class II and/or class III tooth mobility; bone loss (e.g., horizontal and/or vertical); and loss of over $\frac{1}{3}$ of supporting alveolar bone (i.e., crown to root ratio of 2:1 or more). Periodontitis is divided into subdivisions including, but not limited to: adult periodontitis (e.g., plaque-associated); early-onset periodontitis (e.g., prepubertal, juvenile, rapidly progressive and the like); periodontitis associated with systemic diseases; necrotizing ulcerative periodontitis; refractory periodontitis; peri-implantitis and the like.

The term "treating", as used herein, refers to a detectable improvement in an adverse condition and/or a lessening the symptoms of the condition upon contacting a mammal with an oral composition of the invention and/or according to a method of the invention.

The term "treatment of periodontitis" will be understood to include the prevention of periodontitis in a mammal, as well as inhibition of the progression of one or more pre-existing conditions associated with periodontitis in a mammal. As used herein, the terms "inhibit" and "inhibition" refer to a partial inhibition or a complete inhibition of periodontitis compared to the condition without treatment, such that therapeutic treatment and/or prophylaxis results. Treatment of periodontitis according to the invention therefore includes the reduction, inhibition of, improvement of, lessening, diminishment, cessation, or elimination of one or more of the symptoms and/or sequelae set forth herein.

As used herein, "pathological excess" refers to activity above an accepted normal level. For example, a "pathological excess" of matrix metalloprotease activity is a level of matrix metalloprotease activity that is above the level normally found in a non-disease state. As used herein, a "pathological excess of matrix metalloprotease activity" is a level of matrix metalloprotease activity associated with periodontitis.

As used herein, the term "baseline" refers to a level of an agent (e.g., a biomarker) that exists in a subject before an adverse event, or to a level which would exist after therapeutic treatment. A "baseline" level of a biomarker, for example, may be a level of biomarker considered to reflect a "normal" or "healthy" subject. Alternatively, a "baseline" level of a biomarker may reflect the level of a biomarker that exists prior to onset of periodontal disease, wherein the level of biomarker was already elevated above a "normal" or "healthy" level prior to the onset of periodontal disease, due to a condition possibly unrelated to the periodontal disease. In the second example, treatment of the subject to return the level of biomarker back to the "baseline" level can reflect "treatment of periodontitis", despite the fact that the baseline level in this example is elevated above an accepted "healthy" level.

As used herein, the term "down regulate" refers to a decrease in enzymatic activity, a decrease in the level of enzymatic activity, a decrease in the level of protein and/or nucleic acid encoding such protein, or a decrease in the biochemical effect of the presence of a protein, such as one or more of MMP-8, MMP-9, and MMP-13.

The term "gingival sample", as used herein, refers to tissues, cells, fluids obtained from, at or near the gingiva.

"Gingival crevicular fluid" and "GCF", as used herein, refers to the transudate of blood plasma collecting in the gingival crevice produced by leakage from capillaries in the free gingiva.

As used herein, the term "diagnosing" refers to determining or detecting the presence of a particular disease, disorder, medical condition, or risk.

"Pre-gingivitis condition", as the term is used herein, refers to a condition that is not fully-involved gingivitis, but is any condition other than "normal," tending towards gingivitis and a condition from which gingivitis could develop if left unattended to.

As used herein, the term "detecting reagent" refers to a biological or chemical entity. A "detecting agent" may be an additional reagent added to a composition, or it may be an initial component of a composition which acts as a detecting agent (eg., visual FRET antibody techniques).

Some embodiments of the present invention provide methods of identifying a compound useful in treating a disease or condition of the oral cavity, the method comprising: obtaining a first gingival sample from a mammal suffering from a disease or condition of the oral cavity; obtaining a second gingival sample from the oral cavity of said mammal; contacting said first sample with a test compound; contacting said second sample with a positive control, wherein said positive control is a compound known to down-regulate the expression of one or more biomarkers; measuring the extent to which the expression of one or more of said biomarkers is down-regulated by said test compound; measuring the extent to which the expression of one or more of said biomarkers is down-regulated by said positive control; and comparing the extent to which the expression of one or more of said biomarkers is down-regulated by said test compound, with the extent to which the expression of one or more of said biomarkers is down-regulated by said positive control; wherein a test compound that down-regulates the expression of one or more of said biomarkers to an equal or greater extent than said positive control, is a compound useful in treating a disease or condition of the oral cavity.

In some embodiments, the one or more biomarkers are selected from the group consisting of: FAS, IL-1B, IL-8, MMP-9, DEFB4, CTSS, IL-17B, CARD10, BGN, BE, IL-12A, IL-6, LCN8, LPO and MMP-13. In further embodiments, the positive control down-regulates the expression of FAS, IL-1B, IL-8, MMP-9, DEFB4, CTSS, IL-17B, CARD10, BGN, BE, IL-12A, IL-6, LCN8, LPO and MMP-13.

In some embodiments, the disease or condition of the oral cavity is gingivitis or periodontitis.

In some embodiments, the positive control is a halogenated diphenylether. In other embodiments, the positive control is triclosan.

Yet other embodiments provide methods wherein the test compound down-regulates the expression of one or more of said biomarkers to a greater extent than said positive control. In some embodiments, the test compound down-regulates the expression of FAS, IL-1B, IL-8, MMP-9, DEFB4, CTSS, IL-17B, CARD10, BGN, BE, IL-12A, IL-6, LCN8, LPO and MMP-13, to a greater extent than said positive control. In further embodiments, the positive control down-regulates the expression of MMP-9. In still other embodiments, the positive control down-regulates the expression of MMP-13.

In an aspect, the invention features method for diagnosing periodontal disease in a mammal, comprising obtaining a gingival sample from the mammal, detecting the presence of a biomarker in the gingival sample, detecting the level of the biomarker in the gingival sample, diagnosing the organism with periodontal disease based on the level of the biomarker detected. The biomarker is at least one member selected from the group consisting of FAS, IL-1B, IL-8, MMP-9, DEFB4, CTSS, IL-17B, CARD10, BGN, BE, IL-12A, IL-6, LCN8, LPO and MMP-13. In an embodiment, a mammal is a human.

A gingival sample may be obtained by any method now known in the art, or yet to be discovered. That is, the invention is not limited by the method of obtaining a gingival sample. By way of a non-limiting example, a gingival sample may be obtained by obtaining an oral tissue sample from the oral cavity. Gingival samples, including gingival biopsies, are obtainable by routine dental procedures. Oral tissues include, but are not limited to fibroblasts and epithelial cells obtained form the oral cavity, as well as tissue and/or cellular samples obtained from the periodontum and the gingiva.

The skilled artisan will understand how to identify a biomarker in the gingival sample, including a biomarker that is associated with and/or secreted by the gingival sample. An exemplary method for detecting the presence of a biomarker comprises obtaining a gingival sample from the oral cavity of a test subject and contacting the sample with a compound or an agent capable of detecting one or more of the biomarkers (e.g., MMP-9, or MMP-13) described herein, e.g., biomarker nucleic acid (e.g., mRNA, genomic DNA, among others) or biomarker peptide (e.g., peptide fragment or protein, among others) encoded by the biomarker nucleic acid such that the presence of a biomarker nucleic acid or biomarker peptide encoded by the nucleic acid is detected in the biological sample. In an embodiment, an agent for detecting biomarker mRNA or biomarker genomic DNA is a labeled nucleic acid probe capable of hybridizing to biomarker mRNA or genomic DNA. The nucleic acid probe can be, for example, a full-length biomarker nucleic acid or a portion thereof. Other suitable probes for use in the diagnostic assays of the invention are described herein.

In another embodiment, an agent for detecting biomarker peptide is an antibody capable of binding to a biomarker peptide, such as an antibody with a detectable label. Antibodies can be polyclonal or monoclonal. An intact antibody, or a fragment thereof (e.g., Fab or F(ab')$_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

As the term is used herein, "gingival sample" (as well as the term "biological sample") is intended to include tissues, cells and biological fluids isolated from the oral cavity of a subject, as well as tissues, cells and fluids present within the oral cavity of a subject. A saliva sample may or may not contain some or all of the same components as a gingival. That is, the detection method of the invention can be used to detect biomarker mRNA, peptide (e.g., protein), or genomic DNA in a biological sample in vitro as well as in vivo. By way of a non-limiting example, in vitro techniques for detection of biomarker mRNA include Northern hybridizations and in situ hybridizations. In vitro techniques for detection of biomarker peptide include enzyme linked immunosorbent assays (ELISAs), Western blots, immunoprecipitations and immunofluorescence. In vitro techniques for detection of biomarker genomic DNA include Southern hybridizations. In vivo techniques for detection of biomarker peptide include introducing into the oral cavity of a subject a labeled anti-biomarker antibody. For example, the antibody can be labeled with a radioactive biomarker whose presence and location in a subject can be detected by standard imaging techniques.

The level of biomarker can be quantified using any method now known in the art, or yet to be discovered. That is, the invention is not limited by the method of quantifying a biomarker. Methods for quantification of a biomarker may include those methods set forth elsewhere herein for detection of the biomarker, or the appropriate modification of such methods, as will be understood by the skilled artisan. In an embodiment, an ELISA-based assay is used to quantify a biomarker (E.g., use of a $PGE_2$ to quantify IL-1B). In another embodiment, a flow cytometery-based method is used to quantify a biomarker (E.g., LUMINEX technology, including flow cytometry and laser-based detection).

In an aspect, a mammal is diagnosed with periodontal disease when a biomarker selected from the group consisting of FAS, IL-1B, IL-8, MMP-9, DEFB4, CTSS, IL-17B, CARD10, BGN, BE, IL-12A, IL-6, LCN8, LPO and MMP-13 is elevated over that level which is considered as "normal" in the art. It will be understood that a "normal" level of any given biomarker may be a singular value, or it may actually be a range of concentrations of the biomarker. A "normal" level of a biomarker is that which is associated with a healthy state, or a state of health devoid, or substantially devoid, of periodontal disease. Such values and ranges may be known in the art, or may be ascertained by the skilled artisan using methods known in the art, including, but not limited to, conducting biomarker detection assays on gingival samples obtained from a subject population of mammals known not to have periodontal disease, or alternatively, symptoms of periodontal disease. In another embodiment, a "normal" level/range of a biomarker for a specific mammalian subject may be determined for that specific mammalian subject at a time when the mammalian subject is known not to have periodontal disease, or alternatively, symptoms of periodontal disease.

A "normal" level, value, or range of a biomarker may be used as a predetermined reference value for the absence, or substantial absence of periodontal disease in a mammal. In another aspect, a value above a normal value or range of a biomarker may be used as a predetermined reference value for the presence of periodontal disease in a mammal.

In an embodiment, a method for diagnosing periodontal disease in a mammal comprises obtaining a gingival and/or saliva sample from the mammal, detecting the presence of a biomarker in the sample, detecting the level of the biomarker in the sample, and comparing the level of biomarker in the sample to predetermined reference value correlating a level of biomarker with periodontal disease; and diagnosing the mammal with periodontal disease when the level of the biomarker in the sample corresponds to the level of biomarker that the reference value correlates with periodontal disease, wherein the biomarker is at least one member selected from the group consisting of FAS, IL-1B, IL-8, MMP-9, DEFB4, CTSS, IL-17B, CARD10, BGN, BE, IL-12A, IL-6, LCN8, LPO and MMP-13. In an embodiment, the periodontal disease is periodontitis. In another embodiment, the periodontal disease is gingivitis.

In another embodiment, a method for diagnosing periodontal disease in a mammal comprises obtaining a gingival and/or saliva sample from the mammal, detecting the presence of a biomarker in the sample, detecting the level of the biomarker in the sample, comparing the level of biomarker in the gingival and/or saliva sample to the level of the same biomarker in a control sample, wherein the mammal is diagnosed with periodontal disease when an altered level of the biomarker is detected in the gingival and/or saliva sample relative to the control sample, wherein the biomarker is at least one member selected from the group consisting of FAS, IL-1B, IL-8, MMP-9, DEFB4, CTSS, IL-17B, CARD10, BGN, BE, IL-12A, IL-6, LCN8, LPO and MMP-13. In an aspect, the level of biomarker is greater in the gingival and/or saliva sample relative to the control sample. In an embodiment, the periodontal disease is periodontitis. In another embodiment, the periodontal disease is gingivitis.

The invention also provides a panel of biomarkers for detecting periodontal disease in a mammal comprising two or more biomarkers selected from the group consisting of FAS, IL-1B, IL-8, MMP-9, DEFB4, CTSS, IL-17B, CARD10, BGN, BE, IL-12A, IL-6, LCN8, LPO and MMP-13, wherein the biomarkers are obtained from a gingival and/or saliva sample of a mammal diagnosed with periodontal disease. In an embodiment, the periodontal disease is periodontitis. In another embodiment, the periodontal disease is gingivitis.

The invention also includes a method for monitoring periodontal disease in a mammal comprising obtaining a first gingival and/or saliva sample from the mammal at a first point in time, obtaining a second gingival and/or saliva sample from the mammal at a second point in time, detecting the presence of at least one biomarker in the first and second samples, detecting the level of the at least one biomarker in the first and second gsamples, and comparing the level of biomarker in the first and second samples, wherein a decrease of the level of the biomarker in the second sample relative to the first sample indicates a decrease in periodontal disease in the mammal, and wherein the at least one biomarker is selected from the group consisting of FAS, IL-1B, IL-8, MMP-9, DEFB4, CTSS, IL-17B, CARD10, BGN, BE, IL-12A, IL-6, LCN8, LPO and MMP-13. In an embodiment, the periodontal disease is periodontitis. In another embodiment, the periodontal disease is gingivitis.

In an aspect, the invention features a method for treating periodontal disease in a mammal, wherein the mammal has an elevated level of at least one biomarker selected from the group consisting of FAS, IL-1B, IL-8, MMP-9, DEFB4, CTSS, IL-17B, CARD10, BGN, BE, IL-12A, IL-6, LCN8, LPO and MMP-13. As described elsewhere herein, above-normal levels of one or more such biomarkers can be determined using any method disclosed herein or known in the art, and correlated with periodontal disease as appropriate. The invention therefore features a method for treating periodontal disease in a mammal having periodontal disease, the method comprising contacting a cell with an agent that down-regulates at least one biomarker selected from the group consisting of FAS, IL-1B, IL-8, MMP-9, DEFB4, CTSS, IL-17B, CARD10, BGN, BE, IL-12A, IL-6, LCN8, LPO and MMP-13, wherein the down-regulation of the biomarker correlates with a reduction in at least one symptom associated with the periodontal disease.

In an embodiment, a biomarker down-regulating agent is comprised within an oral composition, and the oral composition is administered to a mammal to treat the periodontal disease.

In a method of treating periodontitis by administering to the oral cavity of the mammal an oral composition, the activity of one or more biomarkers may be reduced as described elsewhere herein. One or more biomarkers may be reduced as described elsewhere herein, for example, as set forth for reduction in the amount of MMP-9 in the oral cavity of a mammal with respect to reduction in the amount of MMP-9 in the oral cavity of a mammal. That is, an MMP may be reduced at one or both of the nucleic acid and protein levels, thereby reducing the activity of the MMP-9 in the oral cavity. Similarly, the down-regulation of an MMP-9 or the reduction in the level of an MMP-9 may be effected by action at either or both of the nucleic acid and protein levels, as described in detail elsewhere herein.

In another aspect, the invention provides a method of identifying a compound useful in treating periodontal disease in a mammal in need thereof, comprising contacting a cell with a test compound and determining whether the test compound down-regulates one or more of the biomarkers FAS, IL-1B, IL-8, MMP-9, DEFB4, CTSS, IL-17B, CARD10, BGN, BE, IL-12A, IL-6, LCN8, LPO and MMP-13. The down-regulation of at least one of the biomarkers is an indication that the test compound is useful to treat periodontal disease in a mammal afflicted with periodontal disease, wherein the increased level of the biomarker is associated with and/or symptomatic of periodontal disease. In an embodiment, the periodontal disease is periodontitis. In another embodiment, the periodontal disease is gingivitis.

In one embodiment, a method of treating periodontal disease comprises administering an agent identified by a screening assay described herein, or a combination of agents that inhibit one or more biomarkers of periodontal disease, wherein at least one of the agents is an agent identified by a screening assay described herein.

In an embodiment, the invention provides a method for treatment of periodontal disease, comprising the step of administering a therapeutically effective amount of an agent which inhibits the periodontal disease to a subject in need of such treatment. As defined herein, a therapeutically effective amount of agent (i.e., an effective dosage) ranges from 0.001 to 30 mg/kg body weight, preferably 0.01 to 25 mg/kg body weight, more preferably 0.1 to 20 mg/kg body weight, and even more preferably 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an inhibitor can include a single treatment or, preferably, can include a series of treatments. It will also be appreciated that the effective dosage of in used for treatment may increase or decrease over the course of a particular treatment. Changes in dosage may result from the results of diagnostic assays as described herein. By way of example, the agent is administered alone, as part of a pharmaceutical composition, or as part of an oral composition, among other compositions.

By way of a non-limiting example, the level of MMP-9 may be ascertained in vitro by contacting a cell with TNFα. In an embodiment, a cell is a monocyte. After contacting a cell with TNFα, the level of MMP-9 is detected at either the protein or nucleic acid level. In an aspect, the level of MMP-9 is also ascertained in vitro by contacting a cell with TNFα in the presence of an antibacterial agent. In an embodiment, the antibacterial agent is 2,4,4'-trichloro-2'-hydroxydiphenyl ether. In an aspect of the invention, 2,4,4'-trichloro-2'-hydroxydiphenyl ether is an agent useful to down-regulate a biomarker set forth herein. Assays useful for determining the level of a biomarker include any assay useful for binding and/or functional activity determinations, among others. Examples of such assays include, but are not limited to, LUMINEX-based assays, antibody-antigen assays, peptide cleavage assays, colorimetric assays.

In an embodiment of the invention, a measure of down-regulation of MMP-9 by detecting the level of MMP-9 is ascertained in vitro by contacting a cell with TNFα in the presence of an antibacterial agent and comparing the level of MMP-9 ascertained in vitro by contacting a cell with TNFα in the absence of an antibacterial agent, such as 2,4,4'-trichloro-2'-hydroxydiphenyl ether, wherein the experimental conditions are otherwise identical. A lower level of MMP-9 protein, nucleic acid or enzymatic activity in the presence of antibacterial agent than in the absence of antibacterial agent is an indication that the antibacterial compound down-regulates MMP-9. It will be understood that the other biomarkers of the invention may be assayed in a similar manner. Additionally, MMP-9 or any other biomarker may be assayed for down regulation using any agent useful for this purpose, including, but not limited to, agents identified as useful in treating periodontitis as set forth elsewhere herein.

It will be understood that an in vitro measure of down regulation of a biomarker can be correlated to an in vivo effect, observation or result. By way of a non-limiting example, it will be understood that an in vitro measure of down regulation of MMP-9 can be correlated to an in vivo effect, observation or result. In an aspect, down regulation of MMP-9 measured in vitro is a confirmation of an in vivo observation, including, but not limited to, treatment of periodontal disease, a method of reducing a pathological excess of a biomarker and/or biomarker activity in vivo, and a method of identifying a compound useful to treat periodontal disease and/or reduce a pathological excess of biomarker and/or biomarker activity in vivo. See, e.g., Modeer et al. (1996) J. Clin. Periodont., 23:927-933. In another aspect, down regulation of a biomarker measured in vitro is a predictor of an in vivo result, including, but not limited to, treatment of periodontal disease, a method of reducing a pathological excess of biomarker and/or biomarker activity in vivo, and a method of identifying a compound useful to treat periodontal disease and/or reduce a pathological excess of biomarker and/or biomarker activity in vivo.

In an aspect, the invention provides a method of reducing a pathological excess of at least one of biomarker in the oral cavity of a mammal in need thereof comprising administering to the oral cavity of the mammal an oral composition an agent that down-regulates at least one biomarker selected from the group consisting of FAS, IL-1B, IL-8, MMP-9, DEFB4, CTSS, IL-17B, CARD10, BGN, BE, IL-12A, IL-6, LCN8, LPO and MMP-13, in an amount which is effective for reducing the biomarker level in the oral cavity of the mammal, wherein the inhibition of the biomarker level results in the treatment of periodontal disease. In an embodiment, the invention provides a method of reducing a pathological excess of at least one biomarker, e.g., MMM or MMP-13, in the oral cavity of a mammal in need thereof comprising administering to the oral cavity of the mammal an oral composition comprising 2,4,4'-trichloro-2'-hydroxydiphenyl ether in an amount which is effective for reducing the level of MMP-9 or MMP-13 in the oral cavity of the mammal, wherein the inhibition of the MMP-9 or MMP-13 level results in the inhibition of an excessive degradation of connective tissue matrix protein components.

A biomarker may be reduced in the oral cavity in one of multiple ways, as set forth herein. In an embodiment, a biomarker may be reduced in the oral cavity by down-regulating the biomarker at the nucleic acid level, as set forth elsewhere herein. Such a reduction may result in a reduction in one or more of the nucleic acid encoding the biomarker (e.g., mRNA) and the biomarker protein/enzyme expressed into the oral cavity. Reduction of the mRNA encoding a biomarker, for example, may be effected by one or more of multiple techniques, as will be understood by the skilled artisan, when armed with the disclosure set forth herein. Examples include reducing the transcription of mRNA encoding the biomarker and degradation/elimination of the mRNA encoding the biomarker.

In another embodiment, a biomarker may be reduced in the oral cavity by directly reducing the amount of biomarker protein. Reduction of biomarker protein may be effected by one or more of multiple techniques, as will be understood by the skilled artisan, when armed with the disclosure set forth herein. Examples include binding/complexing of the biomarker via a small molecule inhibitor, inhibition via a natural or biologically-derived molecule, proteolytic degradation of the biomarker, and affinity-based clearance of the biomarker from the oral cavity, among others. An agent that reduces a biomarker may be an agent as described herein, such as 2,4, 4'-trichloro-2'-hydroxydiphenyl ether (TRICLOSAN), or it may be another antibacterial agent. As such, the invention provides methods of treating an individual afflicted with periodontal disease.

In another aspect, the invention provides methods of treating periodontal disease in a mammal in need thereof comprising contacting a cell in the oral cavity of the mammal with an agent that down-regulates a biomarker as set forth herein. According to the invention, the down-regulation of the biomarker correlates with a reduction in at least one symptom associated with periodontal disease.

In an aspect, the ability of an oral composition as set forth herein to treat periodontal disease is ascertained by comparison of the effect of 2,4,4'-trichloro-2'-hydroxydiphenyl ether on biomarker down regulation with the effect of the oral composition on biomarker down regulation. In another aspect, the ability of any oral composition to treat periodontitis is ascertained by comparison of the effect of the oral composition, either in vivo or in vitro, with the effect of an oral composition as set forth herein.

In an aspect, down regulation of a biomarker (e.g., a metalloprotease) measured in vitro is a confirmation of an in vivo observation, including, but not limited to, treatment of periodontitis, a method of reducing a pathological excess of the biomarker (e.g., metalloprotease and/or metalloprotease activity) in vivo, and a method of identifying a compound useful to treat periodontitis and/or reduce a pathological excess of the biomarker or biomarker activity in vivo. See, for example. Golub et al., Inflamm. Res. (1997) 46:310-9, Preshaw et al., J. Clin. Periodontol. (2004) 31:697-707; Mantyla et al., J. Periodontal. Res. (2003) 38:436-439; Lorencini et al., Histol. Histopathol. (2009) 24:157-166; and Pozo et al., J. Periodontal Res. (2005) 40:199-207.

The invention further includes an oral composition, such as a dentifrice, for use in a method of the invention. In an aspect, an oral composition comprises an agent useful for treating periodontal disease. In an exemplary embodiment, the agent is a noncationic antibacterial agent. See, for example, U.S. Pat. No. 5,288,480, which is hereby incorporated by reference in its entirety herein. The noncationic antibacterial agent is present in the oral composition in an effective antiplaque amount of 0.25-0.35% by weight, preferably 0.3%. The antibacterial agent is substantially water-insoluble, meaning that its solubility is less than 1% by weight in water at 25° C. and may be even less than 0.1%. In an embodiment, the antibacterial agent is 2,4,4'-trichloro-2'-hydroxydiphenyl ether. In an embodiment, the antibacterial agent is doxycycline. In another embodiment, the oral composition comprises two or more antibacterial agents. In another embodiment, the oral composition comprises an agent other than an antibacterial agent, and may or may not comprise one or more additional agents that are antibacterial agents.

In an embodiment, an antibacterial-enhancing agent (AEA) enhances delivery of the antibacterial agent to, and retention thereof on oral surfaces. In an aspect, an AEA comprises an adherent material. See U.S. Pat. No. 5,288,480 for descriptions of materials and compositions useful for AEA materials of the present invention, as well as for general descriptions of oral compositions, such as dentifrice compositions, useful in the present invention. By way of a non-limiting example, an adherent material in a composition is a polymer having a number average molecular weight between 100,000 and 2,500,000, inclusive. In an aspect, the adherent material is selected from polymers of polyvinyl phosphonic acid, poly (1-phosphonopropene) sulfonic acid, poly(beta styrene phosphonic acid), alpha styrene phosphonic acid, synthetic anionic polymeric polycarboxylate, maleic anhydride, maleic acid, and methyl vinyl ether. In another aspect, the adherent molecule is a polymer of methyl vinyl ether and maleic anhydride.

As used herein, a "delivery-enhancing group" refers to one which attaches or substantively, adhesively, cohesively or otherwise bonds the AEA (carrying the antibacterial agent) to oral (e.g. tooth and gum) surfaces, thereby "delivering" the antibacterial agent to such surfaces. In another embodiment, the "delivery-enhancing group" refers to one which optionally attaches or substantively, adhesively, cohesively or otherwise bonds an agent other than an antibacterial agent to oral surfaces, thereby "delivering" the antibacterial agent to such surfaces. In yet another embodiment, a "delivery-enhancing group" delivers at least one antibacterial agent and at least one non-antibacterial agent to the tooth. The organic retention-enhancing group, generally hydrophobic, attaches or otherwise bonds the agent and/or antibacterial agent to the AEA, thereby promoting retention of the antibacterial agent to the AEA and indirectly on the oral surfaces. In some instances, attachment of the antibacterial agent occurs through physical entrapment thereof by the AEA, especially when the AEA is a cross-linked polymer, the structure of which inherently provides increased sites for such entrapment. The presence of a higher molecular weight, more hydrophobic cross-linking moiety in the cross-linked polymer still further promotes the physical entrapment of the antibacterial agent to or by the cross-linked AEA polymer.

In an exemplary dentifrice, an orally acceptable vehicle including a water-phase with humectant is present. Water is present typically an amount of at least 3% by weight, generally 3-35% and humectant, preferably glycerine and/or sorbitol, typically total 6.5-75% or 80% by weight of the dentifrice, more typically 10-75%. Although not required in the present invention wherein 0-25-0.35% of the water insoluble non-cationic antibacterial agent is present optionally, an additional ingredient which assists solubilization of the antibacterial agent in saliva may be incorporated in the water-humectant vehicle. Such optional solubilizing agents include humectant polyols such as propylene glycol, dipropylene glycol, and hexylene glycol, cellosolves such as methyl cellosolve and ethyl cellosolve, vegetable oils and waxes containing at least 12 carbons in a straight chain such as olive oil, castor oil and petrolatum and esters such as amyl acetate, ethyl acetate and benzyl benzoate. As used herein "propylene glycol" includes 1,2-propylene glycol and 1,3-propylene glycol. Significant amounts of polyethylene glycol particularly of molecular weight of 600 or more should be avoided since polyethylene glycol effectively inhibits the antibacterial activity of the noncationic antibacterial agent. For instance, polyethylene glycol (PEG) 600 when present with triclosan in a weight ratio of 25 triclosan:1 PEG 600 reduces the antibacterial activity of triclosan by a factor of 10-20 from that prevailing in the absence of the polyethylene glycol.

The pH of an oral composition is generally in the range of 4.5 to 10 and in another aspect, 6.5 to 7.5. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

Any abrasive particulates may be used and may be selected from sodium bicarbonate, calcium phosphate (e.g., dicalcium phosphate dihydrate), calcium sulfate, precipitated calcium carbonate, silica (e.g., hydrated silica), iron oxide, aluminium oxide, perlite, plastic particles, e.g., polyethylene, and combinations thereof. In particular, the abrasive may be selected from a calcium phosphate (e.g., dicalcium phosphate dihydrate), calcium sulfate, precipitated calcium carbonate, silica (e.g., hydrated silica), calcium pyrophosphate and combinations. Any type of silica may be used, such as precipitated silicas or silica gels. Preferred are commercially available silicas such as INEOS AC43, available from Ineos Silicas, Warrington, United Kingdom. Other abrasives may also be used in accordance with the present invention. As set forth in U.S. Pat. No. 4,358,437, powdered forms of calcium carbonate in an abrasive form constitute one important class of such abrasives. Examples of these abrasives are milled limestone or marble, chalks such as aragonite, calcite or mixtures thereof, and synthetically precipitated chalks such as waterworks chalk. Generally, the calcium carbonate should have a weight median diameter of less than 40 microns, preferably less than 15 microns. A second class of abrasives are powdered silicas, particularly, silica xerogels as defined in U.S. Pat. No. 3,538,230. A silica-based component may comprise silica particles having an average particle size from 1-100 µm, including any specific particle size within that range.

In an embodiment, an oral composition optionally comprises a siliceous polishing agent. The polishing agent may be a siliceous material such as a hydrous silica gel, a silica xerogel or a complex amorphous alkali metal aluminosilicate or zirconosilicate or a precipitated silica. Colloidal silica materials include those sold under the trademark SYLOID such as those which have been sold as SYLOID 72 and SYLOID 74. Precipitated silicas include those sold under the trademark ZEODENT such as ZEODENT 113 and ZEODENT 115 and ZEODENT 119. An oral composition may comprise a siliceous polishing agent in an amount from 0-36%. In another embodiment, an oral composition may comprise a siliceous polishing agent in an amount from 0.01-36%.

Without being bound to a theory whereby the advantages of this invention are achieved, it is believed that even in the absence of a special solubilizing material for an antibacterial agent (e.g., 2,4,4'-trichloro-2'-hydroxydiphenyl ether), when the amount of agent is 0.25%-0.35% by weight and a polycarboxylate is present, sufficient agent is present to effect the treatment of periodontitis by way of down-regulation of at least one of MMP-8, MMP-9 or MMP-13. This is equally applicable to other water-insoluble noncationic antibacterial agents herein described.

An oral composition (e.g., dentifrice) may also contain a source of fluoride ions, or fluorine-providing component, as anti-caries agent, in an amount sufficient to supply 25 ppm to 5,000 ppm of fluoride ions. These compounds may be slightly soluble in water or may be fully water-soluble. They are characterized by their ability to release fluoride ions in water and by substantial freedom from undesired reaction with other compounds of the oral preparation. Among these materials are inorganic fluoride salts, such as soluble alkali metal, alkaline earth metal salts, or example, sodium fluoride, potassium fluoride, ammonium fluoride, calcium fluoride, a copper fluoride such as cuprous fluoride, zinc fluoride, barium fluoride, sodium fluorosilicate, ammonium fluorosilicate, sodium fluorozirconate, ammonium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred. Typically, in the cases of alkali metal fluorides, this component is present in an amount up to 2% by weight, based on the weight of the preparation, and preferably in the range of 0.05% to 1%. In the case of sodium monofluorophosphate, the compound may be present in an amount of 0.1-3%, and in an embodiment, 0.7-0.8%.

In an aspect, a composition further comprises an agent selected from a stannous ion agent; a fluoride compound; sodium fluoride; chlorhexidine; alexidine; hexetidine; sanguinarine; benzalkonium chloride; salicylanilide; domiphen bromide; cetylpyridinium chloride (CPC); tetradecylpyridinium chloride (TPC); N-tetradecyl-4-ethylpyridinium chloride (TDEPC); octenidine; delmopinol; octapinol; nisin; zinc ion agent; copper ion agent; essential oils; furanones; bacteriocins, ethyllauroyl arginate, extracts of magnolia, a metal ion source, arginine bicarbonate, honokiol, magonol, ursolic acid, usnic acid, morin, extract of sea buckthorn, a peroxide, an enzyme, a Camellia extract, a flavonoid, a flavan, halogenated diphenyl ether, creatine, and propolis.

EXAMPLES

The invention is further described in the following examples. The examples are merely illustrative and do not in any way limit the scope of the invention as described and claimed.

Example 1

MMP-9 Preparation and Characterization

U937 cells and RPMI 1640 culture medium were obtained from ATCC. Human MMP-9 ELISA Kit (QUANTIKINE) was obtained from R&D Systems. Fetal Bovine Serum (FBS) was obtained from VWR, and the penicillin-streptomycin solution and Tumor Necrosis Factor α (TNFα) were obtained from Sigma.

Human leukemia U937 monocyte lymphoma cells were cultured in RPMI 1640 medium supplemented with 10% FBS and 1% Penicillin-Streptomycin solution. Cells were incubated at 37° C. in a humidified atmosphere containing 5% $CO_2$ and 95% air. Before treatment, cells were transferred into RPMI containing 1% FBS for overnight. Cells were plated on a 48 well plate. Cell culture medium included either TNFα (250 ng/mL), Triclosan (1 ppm), or both agents together or no agent (control). Cells were incubated after treatment for 24 hours. Conditioned media were collected and store at −80° C. until analysis. Samples of conditioned media were subjected to enzyme-linked immunosorbent assays (ELISA) for MMP-9, according to commercial ELISA protocol (FIG. 1).

U937 cells stimulated with TNFα produced an increase in MMP-9 level. Triclosan at 1 ppm significantly reduced MMP-9 level in TNFα stimulated U937 cells.

TABLE 1

Figure 1:
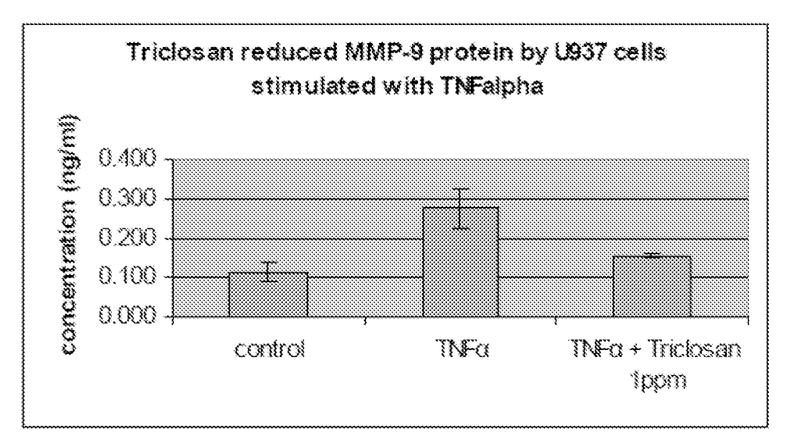
FIG. 1 illustrates the effect of 2,4,4'-trichloro-2'-hydroxydiphenyl ether on TNFα-induced MMP-9 production of monocytes.

Data for FIG. 1, demonstrating the effect of triclosan on MMP-9 production.

|  | Average(ng/ml) | Standard deviation (ng/ml) |
|---|---|---|
| control | 0.114 | 0.024333 |
| TNFα | 0.275 | 0.048665 |
| TNFα + Triclosan 1 ppm | 0.155 | 0.004867 |

Example 2

Preparation and Characterization of MMP-13

Parathyroid hormone (rat PTH 1-34) was purchased from Sigma. UMR 106-01 cells were cultured in Eagle's minimal essential medium (EMEM) supplemented with 25 mM Hepes pH 7.4, 1% nonessential amino acids, 100 units/ml penicillin, 100 μg/ml streptomycin. 5% fetal bovine serum. Real Time Quantitative RT-PCR was conducted according to the following method: UMR 106-01 cells were seeded in 12-well plates and cultured for 2-3 days in cell culture media. When cells were confluent, cell culture media was exchanged with 1% fetal bovine serum for overnight for cell starvation. Cells were pre-incubated with dentifrice for 15 min and then incubated with PTH ($10^{-8}$ M) for 4 hours.

Total RNA was isolated from UMR 106-01 cells stimulated with or without PTH with TRIzol reagent. Total RNA (0.1 μg) was reverse-transcribed to cDNA using the Invitrogen SUPERSCRIPT kit according to the manufacturer's instructions. PCR was performed on cDNA using primers, the sequences of which are set forth in Table 2. All cDNAs were amplified by adding 2.5 μl of cDNA to the PCR mixture (22.5 μl) containing each primer (0.2 μM) and 12.5 μl of the Platinum SYBR Green qPCR SuperMix UDG (Invitrogen). The reactions were preincubated at 50° C. for 2 minutes to decontaminate dU-containing DNA by UDG, then at 95° C. for 2 minutes to inactivate UDG and activate Taq. The PCR program continued 49 cycles of denaturation at 95° C. for 15 seconds, annealing and elongation of the primers at 60° C. for 30 seconds. Relative quantification of gene expression was determined by using the 2-delta delta CT method where fold changes in gene expression are relative to control samples. All samples were normalized to β-actin.

All results were expressed as means±standard error (S.E.) of triplicate measurements with all experiments being repeated at least three times. Statistical analyses were carried out using the Student's t test.

UMR cells stimulated with PTH produced an increase in MMP-13 expression. Triclosan at 10 ppm, 4 ppm and 1 ppm significantly reduced MMP-13 expression in PTH stimulated UMR cells. Dentifrice slurry containing 10 ppm Triclosan significantly reduced MMP-13 expression in PTH stimulated UMR cells.

TABLE 2

Primer Sequences.

Rat MMP-13 gene

5'-GCCCTATCCCTTGATGCCATT-3'  (sense)
5'-ACAGTTCAGGCTCAACCTGCTG-3' (antisense)

Rat-actin gene

5'-AGCCATGTACGTAGCCATCC-3'  (sense)
5'-ACCCTCATAGATGGGCACAG-3'  (antisense)

Example 3

Assay for Anti-Inflammatory Actives

Compounds were assayed for potential anti-inflammatory activity by assaying the ability to inhibit IL-1B, IL-6, IL-8, GM-CSF and/or TNF-α. Cytokines and/or other inflammatory markers found in biological samples (E.g., saliva) or in vitro samples (E.g., cell culture supernatant) were assessed. For example, a percent amount of inhibition at a specific concentration of a marker was generated and used to compare other markers assessed in the same manner.

A cell culture supernatant was prepared from a *Porphyromonas gingivalis*-contacted cell culture. A cell culture can be prepared according to any method known in the art. For example, gingival cells were cultured overnight on a 96-well plate containing 0.5% serum comprising fetal bovine serum (FBS). The next day, media was removed and fresh FBS-free media added and the plate is incubated at 37° C. until further use. Another stock of medium was prepared using heat-killed *Porphyromonas gingivalis* (HKPG) by adding 100 µl HKPG ($10^{10}$/ml stock) to 10 ml medium.

A test agent (e.g., marker) was pre-diluted from a 1% stock by adding 2 µl agent to 198 µl of the media containing $10^8$/ml HKPG. The test agent was then diluted to a final concentration to a final concentration of 1 ppm and 0.5 ppm, using the media containing the HKPG (the mirror plate). A negative control was the medium without HKPG or test agent. A positive control was the medium containing HKPG.

The microplate containing the test agent dilutions was washed once with medium. The conditioned medium from the mirror plate was added to the same sample location on the cell plate, and incubate overnight. The following day, 50 µl medium was removed from each well for use in a flow cytometry-based assay (E.g., LUMINEX).

Reagents were prepared for a LUMINEX 5-PLEX assay. A washing solution was prepared by adding 285 ml deionized water to 15 ml stock wash solution. Assay beads were prepared in a diluted solution by adding 2.25 ml of washing solution to 0.25 ml of a 10× bead stock. Biotinylated antibody, 1×, was prepared by adding 9 ml deionized water to 1 ml of 10× biotinylated detector. Streptavidin-RPE, 1×, was prepared by adding 9 ml deionized water to 1 ml 10× streptavidin-RPE stock.

For the 5-PLEX assay, a standard was prepared by following product instructions, and reconstituting assay diluent (e.g., saliva) or by using 50% assay diluent/50% culture medium. The standard protein was allowed to rehydrate for 10 minutes at room temperature (must be used within one hour). The standard curve was made by serially diluting the reconstituted standard in assay diluent (saliva) or 50% assay diluent/50% culture medium by conducting a series of dilutions to prepare a 1:729 diluted sample.

For the 5-PLEX assay, the plate wells were pre-wetted by pipetting 0.2 ml of wash solution into each well, waiting 15-30 seconds, then aspirating the solution using a vacuum manifold. The diluted bead solution was vortex-agitated for 30 seconds, then sonically treated for at least 30 seconds immediately prior to use in the assay. The diluted bead solution (25 µl) was placed into each well, and kept from light. Wash solution (0.2 ml) was added to each well, and after 15-30 seconds, the wash solution aspirated using a vacuum manifold. The washing step was repeated, then the residual liquid blotted from the bottom of the plate. Incubation buffer (50 µl) was added to each well, followed by 100 µl of the appropriate standard dilution into each designated well, followed by 50 µl assay diluent, then 50µ of sample into the designated sample well. The plate was incubated for 2 hours at room temperature on an orbital shaker with a 500-600 RPM shaking speed.

Liquid was removed from the plate wells using a vacuum manifold, and 0.2 ml wash solution added to the wells, incubated for 15-30 seconds, then the wash step repeated, followed by blotting of the bottom of the plate to dry. Biotinylated detector antibody (1×, 100 µl) was added to each well and the plate incubated for one hour at room temperature on an orbital shaker with a 500-600 RPM shaking speed. Liquid was then removed from the wells using a vacuum manifold, followed by washing, as described above. Streptavidin-RPE (1×, 100 µl) was added to each well. The plate was then incubated for 30 minutes at room temperature on an orbital shaker with a 500-600 RPM shaking speed.

While the plate is incubating, the LUMINEX100 instrument was prepared for the assay. The liquid was removed from the plate wells using a vacuum manifold, and 0.2 ml wash solution added to the wells, incubated for 10 seconds, then the wash step repeated twice. Wash solution (100 µl) was added to each well and the plate incubated for 2-3 minutes at room temperature on an orbital shaker with a 500-600 RPM shaking speed. The plate was then uncovered and inserted into the LUMINEX instrument for reading and analysis.

The concentration of samples from the standard curve was determined using appropriate curve-fitting software. The cytokine inhibition from each concentration of test agent was calculated by first subtracting the level of cytokine with agent from the level of cytokine in the positive control. That value was then divided by the level of cytokine in the positive control, and multiplied by 100, to give the percent inhibition with each particular agent.

A standard curve can also be generated for any marker by plotting the absorbance of various samples of markers of known concentration. The standard curve can then be used to facilitate determination of the concentration of marker in subsequent assays and analysis.

Example 4

Immunochemical Analysis of Markers and Disease State

Antibodies were raised against the following markers: FAS, IL-1B, IL-8, MMP-9, DEFB4, CTSS, IL-17B, CARD10, BGN, IL-12A, IL-6, LCN8, B-factor and LPO. Domain selection for antibody production was performed on criteria including specificity, immunogenicity, hydrophobicity, and cDNA availability. Each target sequence was PCR-amplified from cDNA template and inserted into two prokaryotic expression vectors, one for antigen production and one for affinity ligand production.

Testing with commercially available antibodies was also conducted. Western Blot analysis of commercially available antibodies indicated that IL-6 and MMP-9 were good candidates for additional analysis and testing.

Laying hens (Leghorn and Rhode Island Red) were injected with antigens. Testing samples were collected 10 days post first boost and five days post second boost. Samples were tested using Western Blots or ELISA assays with recombinant proteins/peptides. Antibodies were purified using affinity purification. Cell extracts from Jurkat, A549, HELA, and HEK293 cells were used to test the antibodies.

Antibodies against IL-6, MMP-9 and BFa (B-factor) were used in an immunohistochemical (IHC) study to identify biomarker presence and/or level in tissues correlated with various healthy and diseased states. Gingival tissue specimens were obtained from three subjects having gingivitis (two mild cases and one moderate case). Gingival tissues were also obtained from five subjects having healthy gingiva. Paraffin-embedded formalin-fixed tissue slides were generated for analysis. Multiple swipes were taken from gingivitis tissue source with clinical evidence of inflammation, bleeding, swelling, and changes of surface texture. Healthy gingival source was from tooth removal or crown restoration. Specimen information includes probing depth, tooth number, area and amount of gum harvested. Control tissue was normal bone marrow for IL-6 and BFa, and breast cancer tissue for MMP-9.

MMP-9 showed strong staining in both healthy tissue and tissues with gingivitis. The MMP-9 results may, for example, be combined with data from other biomarkers set forth herein (e.g. data obtained for other MMP's) to produce a particular diagnosis of periodontal disease in a patient. IL-6 only stained in mononuclear cells, consistent with Western blot results (i.e., reacts with Jurkat cells). Correlative trends were also observed for comparisons between healthy and diseased tissue using the anti-IL-6 antibodies and anti-BFa antibodies with the paraffin-embedded tissues, but were not as pronounced as those obtained for MMP-9.

The invention has been described herein by reference to certain preferred embodiments. However, as obvious variations thereon will become apparent to those skilled in the art, the invention is not to be considered as limited thereto. All patents, patent applications, and references cited anywhere is hereby incorporated by reference in their entirety.

What is claimed is:

1. A method of identifying a compound useful in treating a disease or condition of the oral cavity, wherein said disease or condition of the oral cavity is gingivitis or periodontitis, the method comprising:
   obtaining a first gingival sample from a mammal suffering from said disease or condition of the oral cavity;
   obtaining a second gingival sample from the oral cavity of said mammal;
   contacting said first sample with a test compound;
   contacting said second sample with a positive control, wherein said positive control is a halogenated diphenylether compound which is known to down-regulate the expression of one or more biomarkers selected from the group consisting of: FAS, IL-1B, IL-8, MMP-9, DEFB4, CTSS, IL-17B, CARD10, BGN, BE, IL-12A, IL-6, LCN8, LPO and MMP-13;
   measuring the extent to which the expression of one or more of said biomarkers is down-regulated by said test compound;
   measuring the extent to which the expression of one or more of said biomarkers is down-regulated by said positive control; and
   comparing the extent to which the expression of one or more of said biomarkers is down-regulated by said test compound, with the extent to which the expression of one or more of said biomarkers is down-regulated by said positive control;
   wherein a test compound that down-regulates the expression of one or more of said biomarkers to an equal or greater extent than said positive control, is a compound useful in treating said disease or condition of the oral cavity.

2. The method of claim 1, wherein the positive control is triclosan.

3. The method of claim 1, wherein said test compound down-regulates the expression of one or more of said biomarkers to a greater extent than said positive control.

4. The method of claim 1, wherein said test compound down-regulates the expression of FAS, IL-1B, IL-8, MMP-9, DEFB4, CTSS, IL-17B, CARD10, BGN, BE, IL-12A, IL-6, LCN8, LPO and MMP-13, to a greater extent than said positive control.

5. The method of claim 1, wherein said positive control down-regulates the expression of MMP-9.

6. The method of claim 1, wherein said positive control down-regulates the expression of MMP-13.

* * * * *